US012564320B2

(12) United States Patent
Srinivasan et al.

(10) Patent No.: US 12,564,320 B2
(45) Date of Patent: Mar. 3, 2026

(54) APPARATUS AND METHOD FOR SELF-CORRECTING OBJECTIVE REFRACTOMETRY

(71) Applicant: Forus Health Pvt. Ltd., Bangalore (IN)

(72) Inventors: Venkatakrishnan Srinivasan, Bangalore (IN); Revathy Manthri Rangaraj, Bangalore (IN); Subhajit Banerjee Purnapatra, Bangalore (IN); Keerthighaan Kanagasegar, Bangalore (IN)

(73) Assignee: FORUS HEALTH PVT. LTD., Bangalore (IN)

( * ) Notice: Subject to any disclaimer, the term of this patent is extended or adjusted under 35 U.S.C. 154(b) by 500 days.

(21) Appl. No.: 18/004,191

(22) PCT Filed: Jul. 8, 2021

(86) PCT No.: PCT/IN2021/050667
§ 371 (c)(1),
(2) Date: Jan. 4, 2023

(87) PCT Pub. No.: WO2022/009233
PCT Pub. Date: Jan. 13, 2022

(65) Prior Publication Data
US 2023/0263390 A1 Aug. 24, 2023

(30) Foreign Application Priority Data
Jul. 8, 2020 (IN) ............................. 202041029021

(51) Int. Cl.
| | | |
|---|---|---|
| A61B 3/10 | (2006.01) | |
| A61B 3/00 | (2006.01) | |
| A61B 3/103 | (2006.01) | |

(52) U.S. Cl.
CPC ............ *A61B 3/103* (2013.01); *A61B 3/0016* (2013.01); *A61B 3/0091* (2013.01)

(58) Field of Classification Search
CPC ...... A61B 3/103; A61B 3/0016; A61B 3/0091
USPC ....................................................... 351/205
See application file for complete search history.

(56) References Cited

U.S. PATENT DOCUMENTS

| | | | | |
|---|---|---|---|---|
| 10,890,767 | B1 * | 1/2021 | Fernandez | ............. A61B 3/103 |
| 2009/0079938 | A1 * | 3/2009 | Blum | ................. B29D 11/0073 |
| | | | | 351/216 |
| 2018/0263488 | A1 | 9/2018 | Pamplona et al. | |
| 2020/0174284 | A1 | 6/2020 | Chan et al. | |

* cited by examiner

*Primary Examiner* — Mahidere S Sahle
(74) *Attorney, Agent, or Firm* — The Belles Group, P.C.

(57) ABSTRACT

Objective refraction error measuring apparatuses are known. Once the measurement is done, there is no known method for confirming if the measurements are correct. Disclosed is an apparatus wherein once the error is measured, the determined values of the error are used to set the characteristics of a tunable lens so as to correct the error in the vision of the subject. The objective error is measured again while the subject viewing through the tunable lens so set. Objective refraction error is again measured. If the error measured is now within predefined limits, the first measurement is deemed correct and the values are out put so that glasses with those values may be prescribed to the subject.

9 Claims, 4 Drawing Sheets

Reference        Normal        Spherical Error        Astigmatism

APPARATUS AND METHOD FOR SELF-CORRECTING OBJECTIVE REFRACTOMETRY

CROSS-REFERENCE TO RELATED PATENT APPLICATIONS

The present application is a U.S. national stage application under 35 U.S.C. § 371 of PCT/IN2021/050667, filed Jul. 8, 2021, which claims priority to Indian Patent Application No. number 202041029021 filed on Jul. 8, 2020. The disclosures of the aforementioned priority applications are incorporated herein by reference.

TECHNICAL FIELD

This disclosure belongs to the field of medical ophthalmic test instruments. In particular it belongs to the field of measuring refraction of a subject's eyes, and within which, it concerns itself with the field of objective measurement of refraction of a subject's eyes.

BACKGROUND

Human eyes are susceptible to errors in refraction, causing problems in the subject's vision. The most basic errors are myopia (also known as short sight), hypermetropia (long sight or far sight) and astigmatism (cylindrical error). A subject's vision may suffer from one or more of these errors at the same time.

Basic refraction error measurement of the human eye consists of determining three main parameters, as follows:

The magnitude of the spherical error. The unit of measurement is diopter. It is the refractive power of a lens which is equal to the reciprocal of the focal length of the eye, measured in meters;

The magnitude of astigmatism in diopter; and

The astigmatic angle in degrees from the vertical.

These errors can often be caused by refraction errors of the cornea or the crystalline lens or both. Determining the values of these refraction errors, is essential for prescribing corrective glasses. Broadly, there are two approaches to performing such measurements. While subjective refraction tests necessitate the active participation of the patient in the form of feedback about visual clarity, objective tests employ an apparatus to directly estimate the error. Comparison between the benefits of either approach over the other can be found in scientific literature. Both approaches have been widely practiced for decades.

Modern practices generally employ objective refractors first, such as automatic eye refractometers or auto-refractometers to obtain the refractive power of the patient's eyes. These readings are used as starting estimates for performing subjective refraction tests, which would otherwise be a time-consuming process. The final prescription for corrective glasses is thus based on subjective tests obtained with the assistance of results from objective tests.

The basic method used by most auto-refractometers is to project a light pattern into the eye of the subject, imaging the reflections from the fundus of the eye and comparing the image with a reference image to compute the optical power of the eye. A typical, modern apparatus includes projection optics for generating and projecting an infrared light pattern through the pupil of the eye onto the retina. Imaging optics then collect the reflection from the retina, emerging out of the pupil, and focus them onto a photoelectric array device. The output of the array device is digitally processed to compute the refractive power of the eye. To avoid device induced accommodation of the eye, a viewing target with a projected pattern for the subject to fix the gaze on, may also be used.

In state of art auto-refractometers once the refractive powers are estimated, they are not validated in any way. If the objective measurement has error, it will propagate into the subjective refraction process and lengthens the testing time. Further, small axial misalignments in the projection optics may change the shape of the pattern projected on the retina and the refractometer may erroneously compute a refractive power. Periodic calibration is needed to minimize such occurrences. Such calibration may require much effort, is expensive and may render the apparatus unusable during calibration.

SUMMARY

It is thus one of the objects of the present disclosure to mitigate at least one of the problems in the prior art. This disclosure discloses an objective refraction testing apparatus, for example an auto-refractometer that may overcome at least some of the problem of the state of the art, namely the lack of validation of the results of the test.

Towards this, a tunable lens is provided. The lens is first set to a value such that it does not contribute to the objective refraction test in any manner while an initial refractometry is conducted, in a known manner. Once the error in refraction has been calculated, the value is used to set the power of the tunable lens to correct the error in refraction. Refractometry is conducted once again in the usual manner. If the initial measurements were correct, refractometry conducted after setting the tunable lenses to the required value, the values obtained will be the same as the one if the subject's eyes do not have refraction error. This confirms that the original value was correct and thereby it validates the first measurement. If this is not the case, an operator may check the setting up of the apparatus to avoid misalignment, and other such errors, that could have caused the error in the refractometry measurements. Once, the errors have been set right, refractometry may be conducted once again to obtain correct values.

Thus, disclosed is an objective refraction error measuring apparatus for measuring a refraction error in a subject's vision, the apparatus comprising a first computational device for computing a first refraction error in the subject's vision, the apparatus characterized by: a tunable lens; a second computational device configured for computing and setting one or more tuning signals for applying to the tunable lens for setting a refractive characteristic of the tunable lens for substantially nullifying the refraction error in the subject's vision, wherein the one or more signals are computed based on the computed refraction error in the subject's vision; and measuring the refraction error in the subject's vision, through the tunable lens for ascertaining that the error is substantially nullified, for confirming the first computed refraction error in the subject's vision.

This method for measuring the refraction error in the subject's vision may also be referred to as automated objective refractometry with feedback.

An objective refraction error measuring apparatus for measuring a refraction error in a subject's vision, the apparatus comprising a first computational device for computing a first refraction error in the subject's vision, the apparatus comprising a tunable lens, a second computational device configured for computing and setting one or more tuning voltages signals for applying to the electrically tunable lens for setting a refractive characteristic of the tunable lens for substantially nullifying the refraction error in the subject's vision, wherein the one or more signals voltages are calculated based on the computed refraction error in the subject's vision, and measuring a refraction error in a subject's vision through the tunable lens for ascertaining that the error is substantially nullified, for confirming the first computed refraction error in the subject's vision.

Also disclosed is a method for measuring an objective refraction error in a subject's vision, the method comprising: a step of a first objective refraction error measurement of an unaided eye of a subject for determining one or more first values of an error in the subject's vision, a step of controlling a tunable lens, based on the values of the error in the subject's vision determined for correcting the error in the subject's vision, a step of carrying out a second objective refraction error measurement of the subject's vision for determining one or more second values of the refraction error in the subject's vision while the subject is viewing through the tunable lens, a step of comparing the one or more second values of the refraction error in the subject's vision with predetermined limits of refraction error values, and a step of outputting the one or more first determined values of refraction error in the subject's vision when the second determined values are within the predetermined limits.

The summary above is illustrative only and is not intended to be in any way limiting. Further aspects, exemplary embodiments, and features will become apparent by reference to the drawings and the following detailed description.

BRIEF DESCRIPTION OF THE FIGURES

These and other features, aspects, and advantages of the exemplary embodiments can be better understood when the following detailed description is read with reference to the accompanying drawings in which like characters represent like parts throughout the drawings, wherein.

DETAILED DESCRIPTION

For the purpose of promoting an understanding of the principles of the invention, reference will now be made to the embodiments illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not comprise only those steps but may comprise other steps not expressly listed or inherent to such process or method. Similarly, one or more apparatuses or sub-systems or elements or structures or components proceeded by "comprises . . . a" does not, without more constraints, preclude the existence of other apparatuses or other sub-systems or other elements or other structures or other components or additional apparatuses or additional sub-systems or additional elements or additional structures or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

In addition to the illustrative aspects, exemplary embodiments, and features described above, further aspects, exemplary embodiments of the present disclosure will become apparent by reference to the drawings and the following detailed description.

Figure 1:
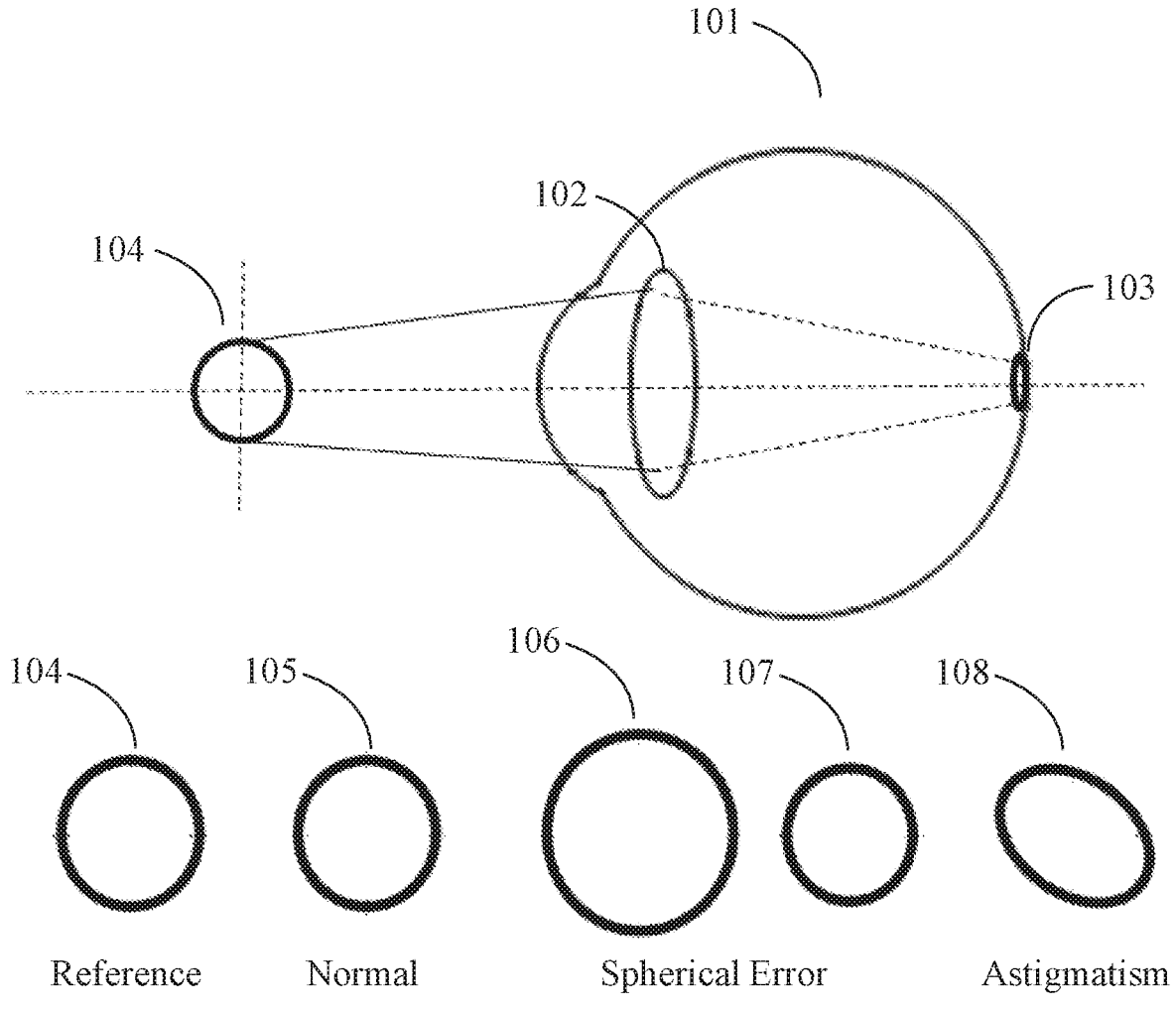
FIG. 1 diagrammatically illustrates the refraction errors in the human eye.

To describe the disclosed apparatus, the basic vision errors will be described with reference to FIG. 1. It shows the cross section of the human eye 101. It has a lens 102 and at the other end a retina 103. When a visual stimulus, say a circle 104, is viewed by the eye, the light rays undergo refraction in the lens 102 of the eye 101 and forms an image on the retina 103. In a normal eye, the image on the retina 103 is also a circle but may be of a different diameter. It can, however, be normalized to the reference stimulus and treated as having the same size as the stimulus image 104. This is as indicated by the circle 105. If the eye has the error myopia the image will be a circle of a larger diameter as shown in 106. On the other hand, if the error is hypermetropia, the image on the retina 103 will be of a smaller diameter as shown by 107. If the eye has the error astigmatism, the image on the retina 103 will be an ellipse and the major axis of the ellipse may be tilted at an angle from the vertical, as shown by 108. The extent to which astigmatism distorts the image is measured in diopters. Often, astigmatism occurs concurrently with myopia or hypermetropia. This figure shows a simplified representation of the errors in refraction in the human eye and but suffices to understand the disclosed apparatus and method.

With the basic understanding of the human eye and the errors in refraction, as described above, the disclosed apparatus will now be described below with reference to FIG. 2. The disclosed apparatus will now be referred to as the objective refraction unit 200. The objective refraction unit 200 includes a pattern generation unit 210. The pattern generation unit 210 produces an illuminated pattern using a light source and lenses for projecting the pattern on to the subject's eye 201. It is to be noted here that the eye is not a part of the disclosed apparatus but included in FIG. 2 to aid the description.

Further, a beam splitter 215 lets the projected beam pass and reach the eye 201 of the subject and redirects the image formed on the retina of the eye 201 to reach an electronic screen 220. The imaging optics includes a combination of lenses to create an image of the image formed on the retina of the eye 201 on an electronic screen 220 for converting the received image into its corresponding digital representation. A charge coupled device (CCD), as the ones used in digital cameras, is but one example of such an electronic screen. The output of the electronic screen 220 is fed to a computational device 225 for image processing for determining the refraction error of the subject's eye 201. The optical part of the objective refraction unit; that is, the part without the computational device 225, is shown as 202 within a dotted lined rectangle and may be referred to as the optical unit 202.

The computational device 225 is configured for receiving data from the electronic screen, analyze the received image, compare the received image with an image expected from an eye without refraction error, and compute the magnitude of the error in the eye 201 of the subject who is under test. It is configured for computing the magnitude of the spherical error, the magnitude of the cylindrical error and its angle.

Figure 2:
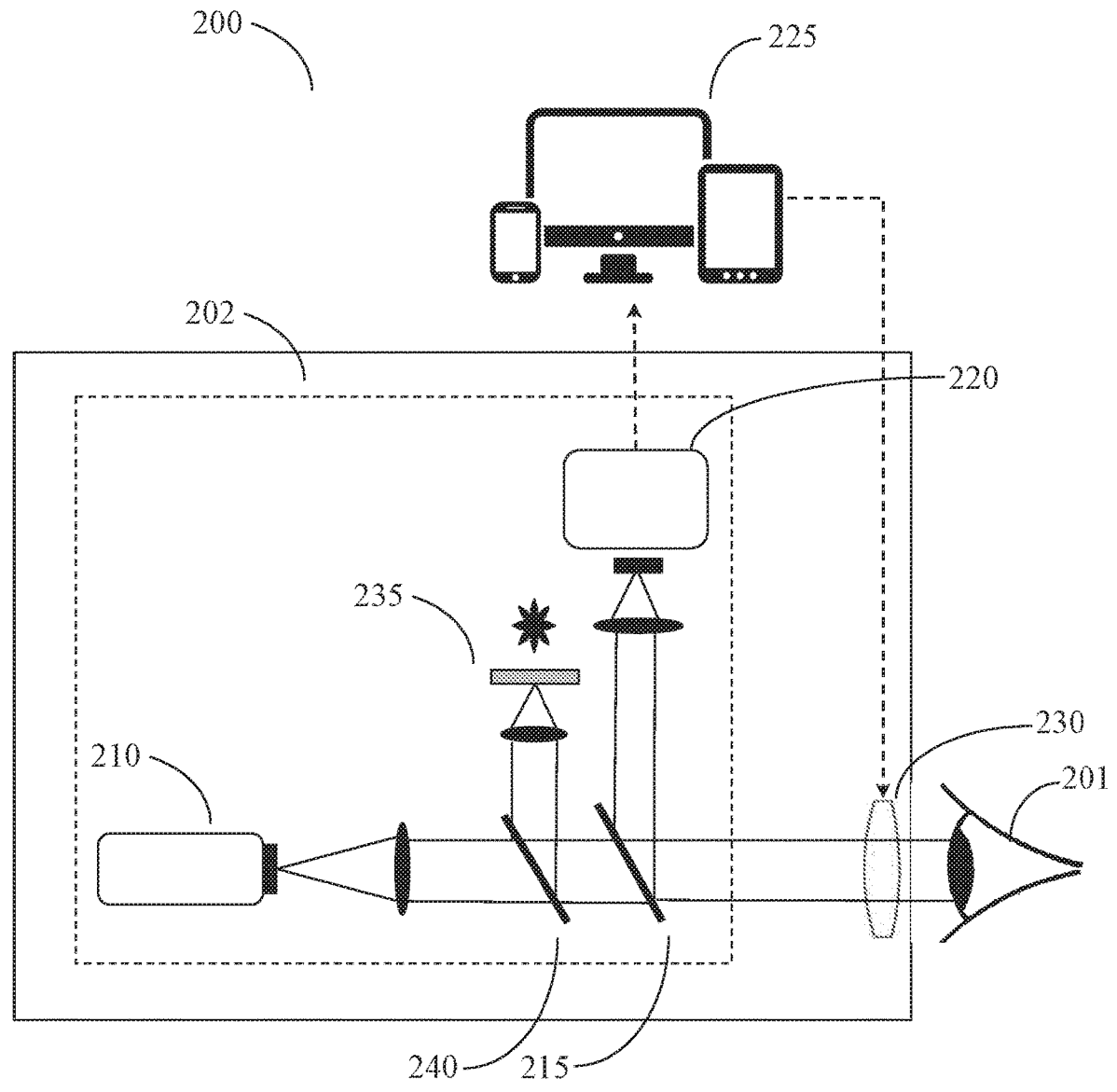
FIG. 2 illustrates the principle of working of the disclosed refractometer.

The description given hitherto with reference to FIG. 2 may be available in known objective refraction apparatuses. What is described hereinafter are particular to this disclosure. The disclosed objective refraction unit 200 comprises a tunable lens 230. Tunable lenses, as is well known, are lenses whose refraction characteristics may be altered through various means, applying electrical voltages to the electrodes of the lens, for instance. Alternatively, tunable lenses wherein mechanical stresses are applied to the lens to alter their optical characteristics are known. The mechanical stresses may be generated using a system of electric motors, shafts, worm, and screw arrangements, and so on. These and other tunable lenses are a part of this disclosure. The apparatus functions as follows. The stimulus is projected to the eye 201 of the subject by the pattern generation unit 210. The image on the retina of the subject's eye 201 is captured by the electronic screen 220 and output to the computational device 225. The computational device 225 compares the image on the retina with an expected image from a refraction error free eye, for measuring the refraction error of the eye 201 of the subject.

Once the error is quantified, the computational device 225 initiates actions to alter the optical characteristics of the tunable lens 230 in such way as to correct the error in the eye 201 of the subject. For the sake of understanding and simplicity, only an electrically tunable lens is referred to in the description below. An electrically tunable lens is one whose optical characteristics are altered by applying appropriate voltages to its electrodes. It will be evident to those of ordinary skill in the art that, mutatis mutandis, the description applies to other types of tunable lenses as well.

In other words, if the hitherto known objective refraction unit was used for prescribing the corrective glasses to the subject, the lens would have a power corresponding to the one that the computational device 225 sets the tunable lens 230 to. Here, corresponding power means that the lens is set to a value that would be different from that of the prescription glasses. The difference depends on the ratio of the distance between the surface of the prescription lens close to the cornea and the corneas of the eye of the subject and the distance between a corresponding surface of the tunable lens and the cornea of the eye 201 of the subject. This is known in the field as the vertex effect. When the tunable lens 230 is set to the value needed for the subject to have normal vision, the process of projecting the stimulus and measuring the error as already described is repeated. If the objective refraction unit 200 now determines that the vision of the subject's eye 201 is normal, it confirms that the original measurement made, without tuning the tunable lens 230, was indeed, correct. Thus, the disclosed apparatus is an objective refraction unit 200 with self-correction.

It is to be noted, however, that the power of the tunable lens is set to, may not be the same as the one that is prescribed to a subject, based on an objective refraction test. The reason is that the power of the lens for prescription glasses depends on the distance between the eye and the glasses. Normally the prescription glasses worn by a subject will be at a greater distance from the eye than the distance between the tunable lens 230 and the eye 201 of the subject, in the disclosed apparatus 200. Hence, the power to which the tunable lens is set, must be compensated for this difference. This is computed mathematically by the computing device 225, that is to say, taking the vertex effect into consideration.

It must be understood that the tunable lens 230, being in the path between the stimulus generator and the retina 203 of the subject's eye 201. However, the computational device 225 is configured to tuning voltages such that the tunable lens 230 does not alter the vision of the subject when the first objective test is done. This may be referred to as the unaided eye.

Further, it is a known problem that there is a phenomenon called machine-induced accommodation of the subject's eye. This leads to erroneous measurement of the subject's vision through autorefractors. To mitigate this, the disclosed apparatus may also include a feature called the auto-fixation. This facilitates the subject to fix the gaze on a definite point in the field of view. To achieve this, one embodiment of the disclosed apparatus may also include an auto-fixation unit 235. This includes an arrangement similar to the pattern generation unit 210 that produces an image and projects it so that while the measurements are being made the subject may fix the gaze on the projected pattern. The pattern is generated and directed to the subject's eye using a second beam splitter 240 as shown in FIG. 2. Once the subject has been instructed suitably to keep looking at this pattern, the measurements of the error in vision first without the tunable lens 230 altering the vision of the subject in any way and then with the tunable lens 230 being operative to compensate for the measured error in the subject's vision may be conducted as described hitherto.

In one embodiment of the disclosed apparatus, the disclosed apparatus is configured as a table-top apparatus. This embodiment may be used as follows. The subject is made to sit on a chair and place the chin in a chin cup and hold the head substantially in the upright position. The height of the chair or the chin cup may be adjustable so that the head can be held in substantially vertical position. In either case, depending on the position of the eye 201, an operator may adjust the vertical and horizontal position of the pattern generation unit 210, the beam splitters 215 and 240 and the tunable lens 230 and the imaging optics 220 to align with the center of the subject's eye 201. It may be preferable to arrange all these elements in fixed positions relative to each other and the operator must only adjust the position of the pattern generation unit 210 to be aligned with the center of the subject's eye 201.

Figure 3:
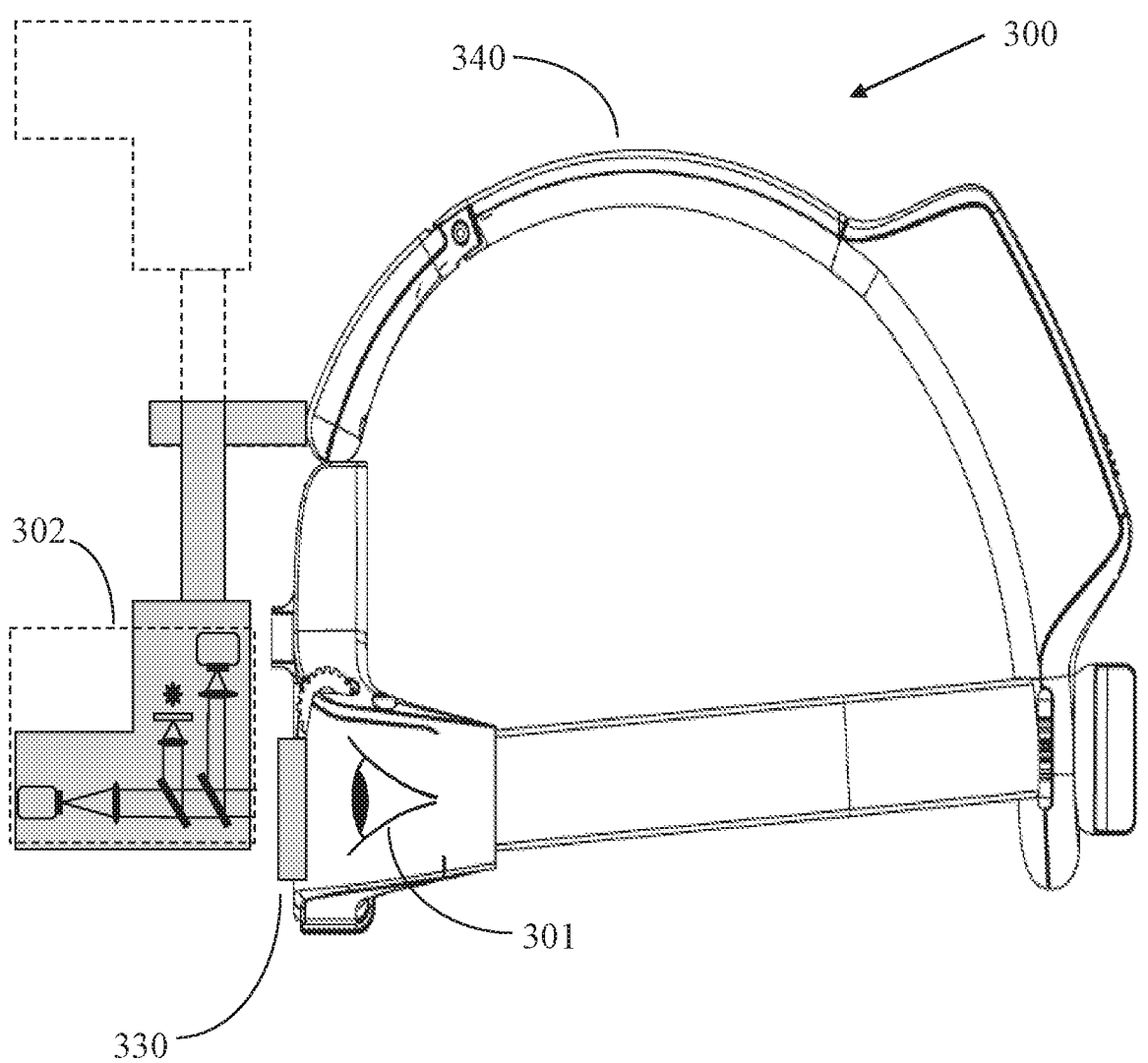
FIG. 3 illustrates an embodiment of the refractometer according to one aspect of this disclosure wherein the refractometer is configured as a head mounted objective auto-refractometer.

In a preferred embodiment, the apparatus is configured as a head mountable unit 300 as shown in FIG. 3. The optical unit 302 is integrated into a headset 340, adapted for being mounted on the subject's head. The harness 340 may be of a form of a helmet, for example. It may also be implemented as a Virtual Reality (VR) headset, for example. The means for communication of signals from the optical unit 302 to the computational device 225 may be implemented with wired connection or wirelessly. The tunable lens 330 is also integrated into the harness 340 such that when the harness is worn by a user, the tunable lens 330 is coaxially in front of the subject's eye 301. Both the optical unit 302 and the tunable lens 330 are mounted in such a way that adjustments that may be needed to make all the relevant elements of the optical unit 302 that need to be coaxial with the subject's eye, the tunable lens 330, can be made.

Still with reference to FIG. 3, in one embodiment of the disclosed apparatus, the optical unit 302 is detachable. This has the advantage that objective refraction test may be conducted as described before with the detachable optical unit attached and once that test and the subsequent confirmation that the first computed refraction error in the subject's vision is indeed correct, the optical unit 302 is detached. This means that the subject is now able to view the scene in front, through the tunable lens and the error in vision is compensated for. With the subject still wearing the head mountable unit, other tests on the subject's vision may be conducted. For instance. Subjective refraction test, field of vision test, color vision test and so on, for example.

Alternatively, the optical unit 302 is mounted in such a fashion that after the subjective refraction test and confirmation that the first computed refraction error in the subject's vision is indeed correct, the optical unit 302 can be moved away so that the subject is able to view the scene in front, through the tunable lens and the error in vision is compensated for. One exemplary way of achieving this would be to assemble the optical unit 302 in a rotatable way as shown with dotted lines in FIG. 3.

If subjective refraction tests are to be conducted, a suitable test chart is displayed to the subject, a Snellen chart or a LogMAR chart, for example. As is well known in the field, a Snellen chart is an eye chart that can be used to measure visual acuity.

Many ophthalmologists and vision scientists now use an improved chart known as the LogMAR chart. Based on the response of the subject reading the alphabets, a user may change the characteristics of the tunable lens, the spherical diopter value, the astigmatism diopter value, and its angle, to complete the subjective refraction test. The final values to which the tunable lens was set to may be output from the computational device as the value of the prescription glasses for the subject. It may also be necessary that the values are modified to account for the vertex effect as described before.

Figure 4:
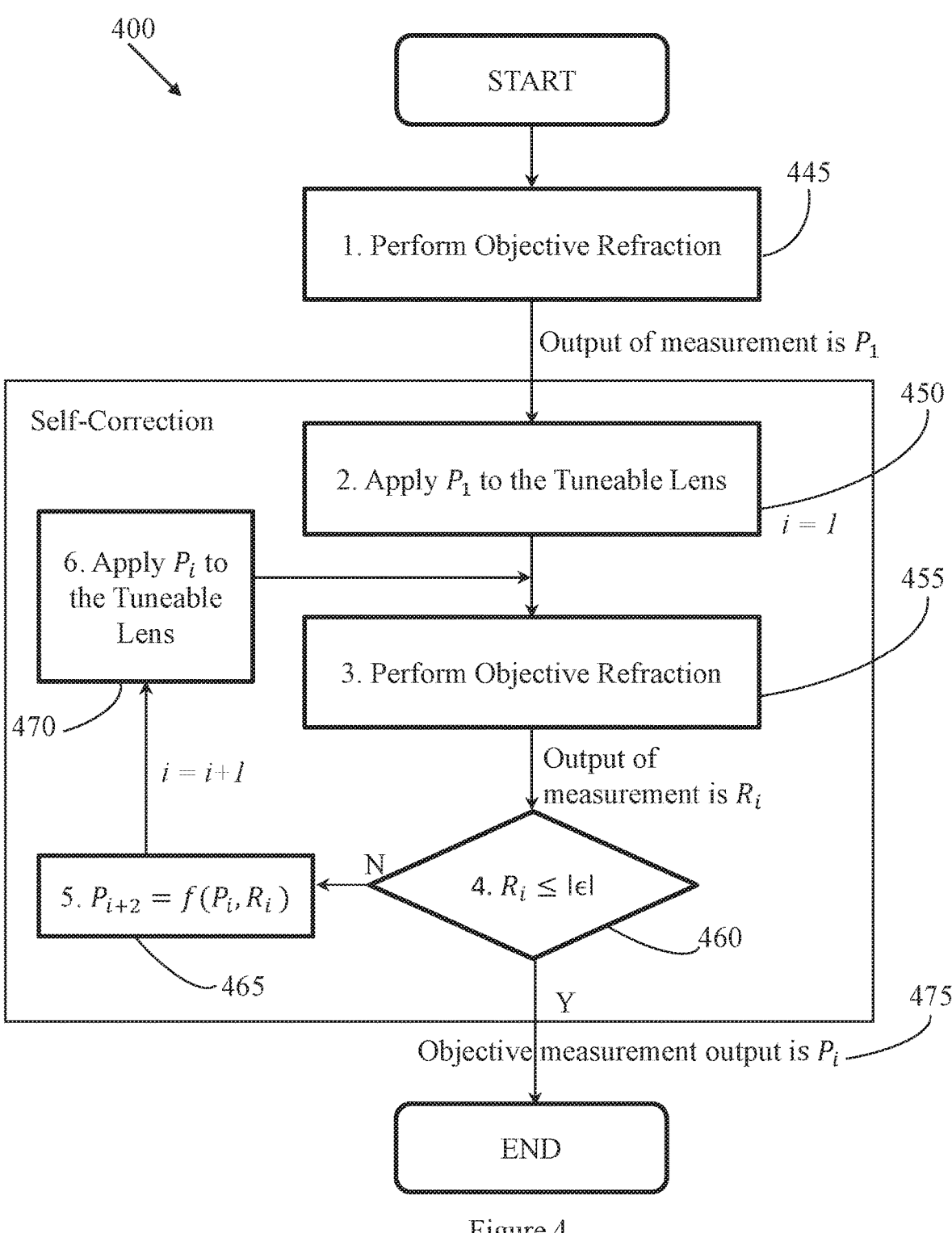
FIG. 4 is a flow diagram of the disclosed method objective refraction with self-correction Further, skilled artisans will appreciate that elements in the figures are illustrated for simplicity and may not have necessarily been drawn to scale. Furthermore, in terms of the construction of the apparatus, one or more components of the apparatus may have been represented in the figures by conventional symbols, and the figures may show only those specific details that are pertinent to understanding the embodiments of the present invention so as not to obscure the figures with details that will be readily apparent to those of ordinary skill in the art having the benefit of the description herein.

Further, a method 400 for self-correcting objective refractometry is disclosed, with reference to FIG. 4. In step 445, a first objective refraction test on the unaided eye of the subject is conducted in a known way. The term unaided eye refers to the subject not wearing any prescription glasses or that the optical characteristics of the tunable lens 230, are set to such a value that it does not change the vision of the subject's eye 201, in any way as described with reference to FIG. 2, is set to; that is, a stimulus in the form of a known pattern, a circle of known diameter is provided to the subject to see. The image formed on the retina of the subject is captured using an electronic screen. The captured image is compared with an image expected from a normal refraction error free human eye and the refraction error of the subject's eye is calculated.

In step 450, a tunable lens is tuned to a value that is expected to correct the refraction error in the subject's eye. At step 455 a second objective refraction test is conducted again. In this case the subject is viewing the stimulus through the tunable lens whose optical characteristics have been tuned or controlled to compensate for the error in the subject's vision. At the comparison step 460, the result of the second objective refraction test is checked to see if the error in refraction of the subject's eye is within predefined limits. If the error is within the predefined limits, in step 475, values of the spherical error or cylindrical error or both are output. If the error is outside the predefined limits, that information that the first refraction error measurement carried out was not reliable is output so that the user, an operator or an optometrist, may check if the apparatus has been set as required and repeat the tests. In this case, properly has the meaning that the axes of the system of lenses of the pattern generation unit and the tunable lens and the crystalline lens of the human eye or on the same line and so on.

In one embodiment of the disclosed method, if the error is outside the predefined limits, a new value for the tunable lens is calculated, based on the results of the first and the second objective refraction tests, and the second objective refraction test is conducted again. The results of the last second refractive test are compared with the predefined limits. If the error is within the predefined limits, in step 475, values of the spherical error or cylindrical error or both are output. If not, steps 465, 470, 455, and 460 are repeated, until the error lies within the predefined limits and the values can be output.

However, if, even after a predetermined number of repetitions of steps 465, 470, 455, and 460 do not yield a refraction error value within the predefined limits, an indication is provided to indicate that the tests were not conclusive. While specific language has been used to describe the disclosure, any limitations arising on account of the same are not intended. As would be apparent to a person skilled in the art, various working modifications may be made to the method in order to implement the inventive concept as taught herein.

The disclosed method may comprise a step of providing a pattern for the subject fix the gaze on, for mitigating errors caused by machine-induced accommodation.

It may be noted that the method described may be implemented in a variety of ways. Even though in the description of the apparatus with reference to FIG. 2 and FIG. 3 is described with a computational device 225 it is possible to carry out at least some of the functions manually or by other means. It is just far more convenient and efficient to configure a computational device to carry out all the steps.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. An objective refraction error measuring apparatus for measuring a refraction error in a subject's vision and confirming the measurement, the apparatus comprising:

an optical unit for projecting a stimulus on an eye of the subject and capturing an image of the stimulus formed on a retina of the eye of the subject;

a tunable lens;

a first computational device for computing a first refraction error in the subject's vision through the tunable lens having no refractive characteristic;

a second computational device configured to:

compute one or more tuning signals and apply the one or more tuning signals to the tunable lens for setting a refractive characteristic of the tunable lens for substantially nullifying the refraction error in the subject's vision, wherein the one or more tuning signals are calculated based on the first refraction error in the subject's vision;

compensate for a vertex distance between the tunable lens and the subject's eye when setting the refractive characteristic of the tunable lens; and measure the refraction error in the subject's vision through the tunable lens for ascertaining that the first refraction error is substantially nullified, for confirming the first refraction error in the subject's vision.

2. The apparatus of claim 1, wherein the first computational device computes the first refraction error in the subject's vision through the tunable lens having no refractive characteristic, by comparing the image of the stimulus formed on the retina of the eye of the subject and an image of the stimulus formed on a retina of a refraction error free eye.

3. The apparatus of claim 1, wherein the apparatus is configured to be wearable by the subject.

4. The apparatus of claim 1, wherein at least one of the first computational device or the second computational device is located remote from the apparatus and is communicatively coupled to the apparatus in one of a wired and a wireless way.

5. The apparatus of claim 1, wherein the second computational device is configured for outputting one or more values of one or more measured values of the refraction error in the subject's vision and characteristics of prescription lenses required by the subject.

6. A method for measuring an objective refraction error in a subject's vision and confirming the measurement, the method comprising:

a step of projecting a stimulus on an eye of the subject and capturing an image of the stimulus formed on a retina of the eye of the subject using an optical unit;

a step of a first objective refraction error measurement of an unaided eye of a subject through a tunable lens having no refractive characteristics, for determining one or more first values of a refraction error in the subject's vision;

a step of controlling the tunable lens, based on the one or more first values of the error in the subject's vision, for correcting the refraction error in the subject's vision, wherein the controlling includes compensating for a vertex distance between the tunable lens and the subject's eye;

a step of carrying out a second objective refraction error measurement of the subject's vision for determining one or more second values of the refraction error in the subject's vision while the subject is viewing through the tunable lens;

a step of comparing the one or more second values of the refraction error in the subject's vision with predetermined limits of refraction error values; and a step of outputting the one or more first values of the refraction error in the subject's vision through the optical unit and the tunable lens when the one or more second values are within the predetermined limits, for confirming that the refraction error is substantially nullified.

7. The method of claim 6, wherein when the one or more second values are outside the predetermined limits, the method comprises:

a step of comparing the one or more second values of the refraction error in the subject's vision with predefined limits of error values; and repeating the steps of controlling the tunable lens, carrying out the second objective refraction error measurement, and comparing the one or more second values of the refraction error in the subject's vision with the predefined limits of error values until the one or more second values of the refraction error in the subject's vision lies within the predefined limits of error values and then outputting the one or more first values of the refraction error in the subject's vision.

8. The method of claim 7, comprising a step of indicating that the refraction error test results are not reliable.

9. The method of claim 7, comprising a step of providing a constant stimulus for the subject to fix gaze on to mitigate errors caused by machine-induced accommodation.

* * * * *